(12) United States Patent
Jackson et al.

(10) Patent No.: US 7,736,352 B2
(45) Date of Patent: Jun. 15, 2010

(54) CLOSURE TAPE TAB FOR ABSORBENT ARTICLE, PRELAMINATED CLOSURE TAPE, AND METHOD OF MANUFACTURING A CLOSURE TAPE

(75) Inventors: Byron M. Jackson, Forest Lake, MN (US); Donald R. Battles, Arden Hills, MN (US); Stuart L. Eynon, Swansea (GB); Dyfrig E. Clement, Llanelli (GB)

(73) Assignee: 3M Innovative Properties Company, St. Paul, MN (US)

( * ) Notice: Subject to any disclaimer, the term of this patent is extended or adjusted under 35 U.S.C. 154(b) by 1002 days.

(21) Appl. No.: 11/339,259

(22) Filed: Jan. 25, 2006

(65) Prior Publication Data

US 2007/0173781 A1  Jul. 26, 2007

(51) Int. Cl.
*A61F 13/15* (2006.01)
(52) U.S. Cl. ............... 604/389; 604/390; 604/391; 604/387
(58) Field of Classification Search .......... 604/389, 604/390, 391, 387, 396, 385.01
See application file for complete search history.

(56) References Cited

U.S. PATENT DOCUMENTS

| | | | |
|---|---|---|---|
| 4,237,890 A * | 12/1980 | Laplanche | 604/390 |
| 5,591,521 A * | 1/1997 | Arakawa et al. | 428/352 |
| 6,063,466 A | 5/2000 | Tuschy | |
| 6,363,587 B1 | 4/2002 | Richter | |
| 6,526,631 B1 | 3/2003 | Alberg | |
| 6,719,744 B2 | 4/2004 | Kinnear | |

FOREIGN PATENT DOCUMENTS

| | | |
|---|---|---|
| EP | 0 247 855 | 12/1987 |
| EP | 0 257 752 | 3/1988 |
| EP | 0 456 472 | 11/1991 |
| EP | 0 482 383 | 4/1992 |
| EP | 0 891 760 | 1/1999 |
| EP | 0 941 730 | 9/1999 |
| EP | 1 002 846 | 5/2000 |
| EP | 1 256 332 | 11/2002 |
| EP | 1 543 807 | 6/2005 |
| WO | WO 96/02218 | 2/1996 |
| WO | WO 01/68025 | 9/2001 |

* cited by examiner

*Primary Examiner*—Jacqueline F. Stephens
(74) *Attorney, Agent, or Firm*—Aleksander Medved

(57) ABSTRACT

The present invention relates to a closure tape tab for an absorbent article, particularly for a disposable diaper, for fastening the article on the body of a person. The closure tape tab comprises a proximal end portion and a distal end portion being connected by an inner tab portion, wherein the inner tab portion has a first major surface and a second major surface. The proximal and distal end portions are connected to the inner tab portion and the first major surface thereof such that opposing ends of the proximal and distal end portions are spaced apart from each other. The distal end portion is folded over toward the proximal end portion such that at least a part of the first major surface of the inner tab portion in the space is covered. The proximal end portion is preferably not folded. The present invention furthermore relates to a prelaminated closure tape, preferably in a stable roll, from which such closure tape tabs can be cut. The closure tape of the present invention is adapted to be level-wound on a roll so that an increased amount of tape can be stored on the roll.

4 Claims, 4 Drawing Sheets

CLOSURE TAPE TAB FOR ABSORBENT ARTICLE, PRELAMINATED CLOSURE TAPE, AND METHOD OF MANUFACTURING A CLOSURE TAPE

FIELD OF THE INVENTION

The present invention relates to a closure tape tab for an absorbent article, particularly for a disposable diaper or an adult incontinence article, for fastening of the article on the body of a person. The invention furthermore relates to a prelaminated closure tape, preferably in a stable level-wound roll, from which closure tape tabs can be cut. Moreover, the present invention relates to a method of manufacturing such a closure tape.

BACKGROUND OF THE INVENTION

A disposable diaper typically has a thin, flexible, stretchy, low density polyethylene backsheet film or a non-woven backsheet, an absorbent core on the inside of the backsheet film and a porous top sheet overlying the core. The diaper is positioned at the crotch of the wearer, two ends of the diaper extending, respectively, towards the front and back. Adjacent edges of the diaper at each side are then either positioned adjacent to each other or overlapped. A closure tape tab is used to close the diaper.

Such a closure tape tab is typically anchored at the diaper to one of its end portions, e.g., the proximal end portion, by means of, for example, a pressure sensitive adhesive layer. The opposite end portion, e.g., the distal end portion, of the closure tape tab comprises a fastening means (e.g., a pressure sensitive adhesive layer or a mechanical fastener component) to close the diaper around the wearer's body and fasten it on the body.

EP-A-0 247 855 relates to a tape fastener laminate on a roll comprising a pressure sensitive adhesive fastener, a central elastic part, a two-part release coated fastening tape and a release tape underneath having an adhesive layer which is covered by a non-tacky film.

EP-A-0 257 752 describes a fastening tape for diapers wound into a roll form for storage. The fastening tape comprises a one-piece backing, a release tape and a pressure sensitive adhesive fastener. The backing has a release coat to allow for unwinding the tape from the roll.

EP-A-0 456 472 discloses an adhesive closure tape having a surface release directly adjacent to an adhesive, wherein an adhesive strip may be coated on a previously release coated area so that the laminate can be wound into a roll.

EP-A-0 482 383 relates to a composite laminate adhesive tape coiled endlessly in roll form, wherein in cross-section the composite laminated adhesive tape is folded in z-form, with the top, slanted and bottom bars of the z-shape being formed by separate first, second and third tape sections of first fastening tape, second central tape and third fastening tape, respectively.

WO 96/02218 describes a two-part fastening tape consisting of a fastening part and a release part and having a pressure sensitive adhesive fastener to be received by the release part when folded over.

EP-A-0 891 760 relates to a closure tape for an absorbent article comprising a backing bearing an adhesive layer, a fastening means and a stretchable elastic sheet. The backing is essentially non-elastic and/or essentially non-extensible. The support sheet comprising the backing and the adhesive layer exhibits one or more incisions in the area of the elastic sheet with at least some of the incisions extending in machine direction over the full width of the backing and the end portion being separated from the incision closest to the end portion by a sufficiently large distance to prevent the incisions essentially from opening and attaching the end portion to the outside surface of the diaper when bending the remaining part of the closure tape to contact the inside of the diaper.

EP-A-1 256 332 discloses a similar construction as the afore-mentioned EP-A-0 891 760, wherein the ratio of the extension of the elastic sheet in the cross-direction over the length of the closure tape prior to fastening it to the absorbent article is between 0.1 and 0.9.

EP-A-0 941 730 describes a fastening tape for diapers with an elastic component as well as with a mechanical fastener, wherein the fastening tape has a backing treated with a release lining. A covering film is arranged to partially cover the adhesive on the lower side of the fastening tape.

EP-A-1 002 846 describes a fastening tape comprising a backing having a fibrous layer of woven fibers or of non-woven fibers of a thermoplastic polymer, wherein the backing comprises on the fibrous layer a silicon release layer and the side of the backing opposite to the side comprising the silicon release layer comprises a pressure-sensitive adhesive layer.

WO 01/68025 describes an elastic laminate tape fastener having a pressure sensitive adhesive element and an expandable fibrous layer which is bonded to an elastic film pointwise to provide for a corrugated structure of the fibrous layer. When stretching the elastic film, the fibrous layer will be brought to its original flat shape and length without stretching it.

EP-A-1 543 807 relates to a closure tape tab for an absorbent article for fastening the article on the body of a person. This closure tape tab comprises a proximal end portion and a distal end portion being connected by an inner tab portion, wherein the inner tab portion has a first major surface and a second major surface. The proximal and distal end portions are connected to the inner tab portion at the first major surface thereof such that the opposing ends of the proximal and distal end portions are spaced apart from each other. An anti-adhesive means is provided at least a part of the first major surface of the inner tab portion in the space. A prelaminated closure tape tab from which such closure tape tabs can be cut is also disclosed. This closure tape is said to be adapted to be level-wound on a roll so that an increased amount of tape can be stored on the roll.

While the known fastening tape tabs are widely used and provide several advantages, there remains a need in the field for further improvements, particularly a need for a closure tape tab for an absorbent article that is adapted to be provided as a prelaminated closure tape that can be supplied in stable roll form by level-winding without the use of additional components that need to be removed prior to the use of the closure tape tab in a diaper manufacturing line and without additional treatment steps.

SUMMARY OF THE INVENTION

In accordance with one aspect of the present invention there is provided a folded closure tape tab for an absorbent article, particularly for a disposable diaper or an adult incontinence article, for fastening of the article on the body of a person. The closure tape tab comprises a proximal end portion and a distal end portion which are connected by an inner tab portion. The inner tab portion has a first major surface and an opposite second major surface, wherein the proximal and distal end portions are connected to the inner tab portion at the first major surface thereof such that opposing ends of the proximal and distal end portions are spaced apart from each other. The distal end portion is folded back on itself toward the proximal end portion such that at least a part of the first major surface of the inner tab portion in the area of the space is covered by the folded part of the distal end portion. Preferably, the proximal end portion is not folded, i.e. substantially straight.

In accordance with another aspect of the present invention there is provided a folded closure tape tab for an absorbent article, particularly for a disposable diaper or an adult incontinence article, for fastening of the article on the body of a person. The closure tape tab comprises a proximal end portion and a distal end portion which are connected by an inner tab portion. The inner tab portion has a first major surface and an opposite second major surface, wherein the proximal and distal end portions are connected to the inner tab portion at the first major surface thereof such that opposing ends of the proximal and distal end portions are spaced apart from each other. The distal end portion is folded back on itself toward the proximal end portion such that at least a part of the first major surface of the inner tab portion in the area of the space is covered by the folded part of the distal end portion. The folded part of the distal end portion preferably comprises a mechanical fastener element and an optional fingerlift.

Preferably, the folded distal end portion substantially covers the space between the opposing ends of the proximal and distal end portions. More preferably, the folded distal end portion covers the space and partially overlaps with the proximal end portion. Advantageously, at least the first major surface of the inner tab portion, preferably both major surfaces of the inner tab portion, are free of a low adhesive backsize coating (LAB).

In accordance with a preferred embodiment of the present invention, a mechanical fastener component is provided on a side of the distal end portion of the closure tape tab that is connected to the inner tab portion. Typically, the mechanical fastener component is arranged towards the free end of the distal end portion. Advantageously, the distal end portion of the closure tape tab comprises a fingerlift adjacent the free end thereof. The fingerlift is preferably provided with a release coating or manufactured from any low surface energy film material. Alternatively, the fingerlift is formed by crushed hooks of the mechanical fastener component provided on the distal end portion. It may also be advantageous to split the distal end portion of the closure tape tab in the area of the fingerlift to provide a gap, wherein the fingerlift is adhesively attached to the distal end portion so that adhesive contact between the fingerlift and the inner tab portion can be established through the gap of the distal end portion. This assists in securing the folded distal end portion in place.

Preferably, the inner tab portion comprises an elastic, an elastic/non-woven composite, or a soft non-woven composite. The proximal and distal end portions and optionally also the inner tab portion are preferably comprised of a non-woven material. The proximal end portion, the inner tab portion and/or the distal end portion may also be made from film materials, particularly polymeric films, paper or other fibrous materials.

According to any of the embodiments of the present invention, the closure tape tab may further comprise a release tape attached to the proximal end portion for securing the closure tape tab to the absorbent article in a so-called Y-bond fashion. The release tape preferably extends at least partially along the second major surface of the inner tab portion. The release tape preferably comprises first and second end sections and an intermediate section connecting the first and second end sections, wherein a surface of the intermediate section directed toward the second major surface of the inner tab portion is provided with an adhesive. This construction provides an anti-flagging feature since the adhesive of the intermediate section attaches the release tape to the inner tab portion so that handling of the closure tape is facilitated.

In accordance with a further aspect of the present invention, there is provided a prelaminated closure tape, preferably in a stable roll, from which closure tape tabs as described above can be cut. A particularly advantageous feature of the present invention is that due to the closure tape tab construction with the folded distal end portion the roll can be level-wound, thus considerably increasing the storage capacity of closure tape material on a roll. Without the distal end portion of the closure tape being folded, these level-wound rolls of closure tape may block because the adhesive provided on the proximal and/or distal end portions and/or on the optional release tape of the closure tape tab would adhere to the first major surface of the inner tab portion of an underlying winding of closure tape. The fact that the proximal end portion is not folded further enhances the stability of the roll, particularly of a level-wound roll. The fact that the proximal end portion is not folded further enhances the stability of the roll, particularly of a level-wound roll. Planetary winding of the closure tape of the invention is of course also feasible.

A further aspect of the present invention relates to a method of manufacturing a closure tape tab from which closure tape tabs for an absorbent article, particularly for a disposable diaper or an adult incontinence article, can be cut so that the closure tape tabs can be used for fastening of the article on the body of a person. This method comprises the steps of providing a first tape section forming a proximal end portion and a second tape section forming a distal end portion of the closure tape tab; connecting the first and second tape sections by means of third tape section forming an inner tab portion, wherein the inner tab portion has a first major surface and an opposite second major surface, and wherein the proximal and distal end portions are connected to the inner tab portion at the first major surface thereof such that opposing ends of the proximal and distal end portions are spaced apart from each other; and folding the distal end portion back on itself toward the proximal end portion such that at least a part of the first major surface of the inner tab portion in the area of the space is covered by the folded part of the distal end portion. The proximal end portion is not folded.

The method of the present invention preferably comprises the additional step of providing a mechanical fastener component on the distal end portion. Advantageously, a fingerlift is provided adjacent the free end of the distal end portion. This fingerlift may be release coated or formed from a low surface energy film material (e.g., a Teflon™ film), or formed by crushed hooks of the mechanical fastener component provided on the distal end portion. Advantageously, the distal end portion is split in the area of the fingerlift to provide a gap, wherein the fingerlift is adhesively attached to the distal end portion so that adhesive contact between the fingerlift and the inner tab portion can be established through the gap of the distal end portion. This helps to secure the folded distal end portion in its position.

It is furthermore preferred to attach a release tape to the proximal end portion, wherein the release tape extends at least partially along the second major surface of the inner tab portion. The release tape is advantageously provided with first and second end sections and an intermediate section, wherein a surface of the intermediate section directed toward the second major surface of the inner tab portion is provided with an adhesive to attach the intermediate section of the release tape to the inner tab portion. This provides an anti-flagging feature, i.e., secures the release tape in place so that the closure tape can be handled easily during manufacturing of the tape and further processing of the closure tape in a diaper manufacturing line.

The connection between the inner tab portion and the proximal and distal end portions is preferably made by ultrasonic welding, cold bonding, thermal pressure bonding and/or adhesive bonding.

According to a further aspect of the present invention, there is provided a method for manufacturing a folded absorbent article comprising the steps of providing a backsheet, a top sheet, an absorbable core therebetween and a closure tape tab as described above, attaching the closure tape tab to an end portion of the absorbent article in its folded configuration, and folding the absorbent article so that a folded part of the distal end portion of the closure tape tab removably engages an opposing end portion of the absorbent article.

An absorbent article manufactured according to the above method is particularly advantageous as during unfolding the folded absorbent article a free end of the distal end portion lifts so that it can be easily seen and grasped by a user.

As already noted above, the present invention is particularly advantageous from a manufacturing point of view since the closure tape tab of the present invention is easy to handle, comprises only a few elements and needs only a few manufacturing steps, and can be stored in a stable roll. A particular advantage of the closure tape of the present invention is that it can be level-wound to a roll on which considerably more closure tape can be stored than on conventional planetary wound rolls. In accordance with the present invention this is achieved without the use of any additional materials that are not necessary for the construction of the closure tape tab as such but assist only in the storing of the tape in roll form such as, for example, the anti-adhesive means described in EP-A-1 543 807.

BRIEF DESCRIPTION OF THE DRAWINGS

In the following preferred embodiments of the present invention will be described in connection with the drawings, in which.

DETAILED DESCRIPTION OF THE PREFERRED EMBODIMENTS

Figure 1:
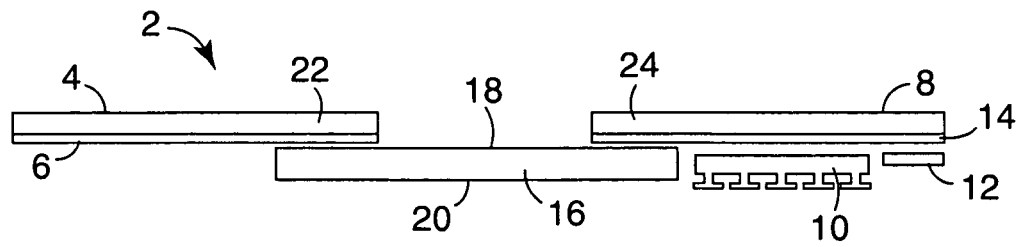
FIG. 1 is a schematic side view of a precursor closure tape tab.

The drawings show the various elements of the closure tape tab and closure tape only schematically. It should be particularly noted that for illustrative purposes some of these elements are shown in the drawings to be slightly apart while they may actually be connected, e.g., by adhesive layers. Moreover, the drawings are not to scale.

In FIG. 1, a precursor closure tape tab 2 is illustrated that can be further processed in order to provide a closure tape tab according to the present invention. The closure tape tab of the present invention is particularly useful for a disposable diaper to which it can be connected at a proximal end portion 4. Typically, the closure tape tab is secured to the diaper by means of an adhesive 6 provided on the lower surface of the proximal end portion 4. The adhesive 6 is preferably provided in the form of an adhesive layer extending substantially along the whole length of the proximal end portion 4, wherein the adhesive layer may be continuous or discontinuous. Furthermore, the adhesive 6 may be applied in the form of a pattern on the lower surface of the proximal end portion 4.

The closure tape tab furthermore comprises a distal end portion 8 opposite to the proximal end portion 4. Accordingly, the proximal end portion 4 constitutes a so-called manufacturer's end of the closure tape tab, while the distal end portion 8 constitutes a so-called user's end of the closure tape tab. The distal end portion 8 comprises an appropriate fastening means, e.g., pressure sensitive adhesive layer or, as illustrated in FIG. 1, a mechanical fastener element 10. Preferably, the mechanical fastener element is provided in a form of a strip with upstanding hooks that are adapted to engage with a loop material provided on a diaper landing area.

Optionally, the distal end portion 8 comprises a fingerlift 12 adjacent a free end thereof so as to allow gripping and opening of the closure tape tab. The mechanical fastener element 10 and the fingerlift 12 are connected to the distal end portion 8 preferably by means of an adhesive 14. The adhesive 14 is provided on a lower surface of the distal end portion 8 and extends preferably along the whole length thereof. As in the case of the adhesive layer 6 on the proximal end portion, the adhesive layer 14 of the distal end portion 8 may be continuous or discontinuous, and may be provided in the form of a pattern.

The proximal end portion 4 and the distal end portion 8 are connected by an inner tab portion 16 having an upper first major surface 18 and a lower second major surface 20. As can be seen in FIG. 1, the proximal and distal end portions 4, 8 are connected to the inner tab portion 16 at the first major surface 18 thereof such that opposing ends 22, 24 of the proximal and distal end portions 4, 8, respectively, are spaced apart from each other.

While the proximal and distal end portions 4, 8 are typically made of an inelastic material, e.g., a non-woven material, the inner tab portion 16 preferably has some elasticity. For example, the inner tab portion 16 may be provided as a laminate comprising an elastic material and an inelastic material limiting the extensibility of the elastic material.

Figure 2:
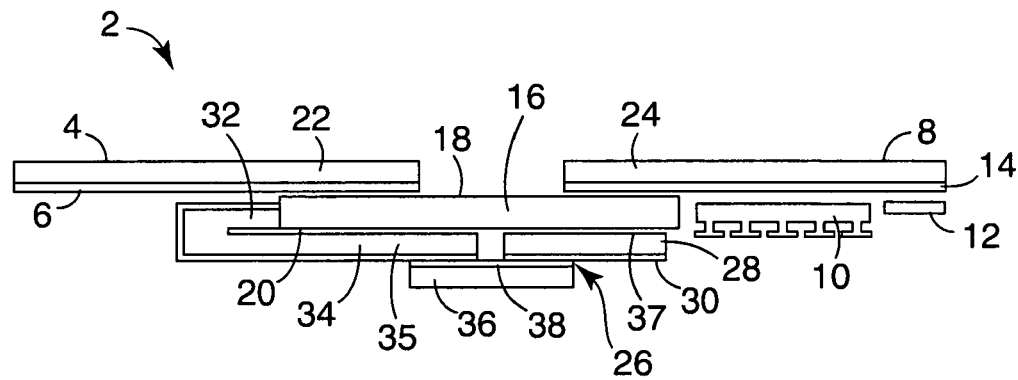
FIG. 2 is a schematic side view of a closure tape tab, similar to the one shown in FIG. 1, with a release tape.
Figure 10:
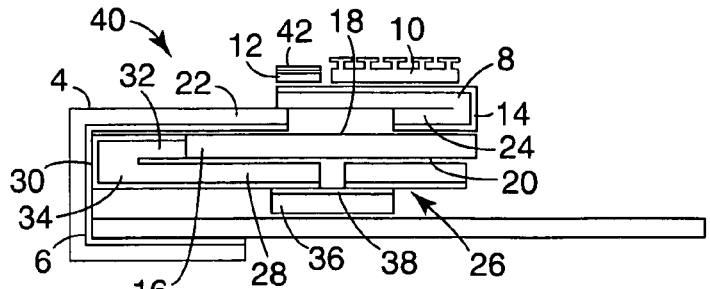
FIG. 10 is a schematic illustration of the attachment of the closure tape tab shown in FIG. 7 at a diaper ear.
Figure 11:
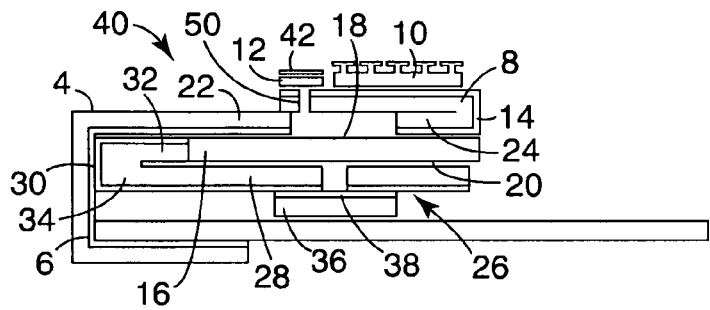
FIG. 11 is a schematic side view of another embodiment of a closure tape tab according to the present invention attached to a diaper ear.

Optionally, the precursor closure tape tab from which the closure tape tab of the present invention can be manufactured comprises a release tape 26 attached to the proximal end portion 4 as shown in FIG. 2. The release tape 26 typically comprises a backing 28 coated on one surface with an adhesive 30. The release tape 26 is preferably attached to the proximal end portion 4 along a relatively short portion 32 of the release tape 26. This short portion 32 is advantageously provided by folding a length of the backing 28 and the adhesive layer 30 back on itself. The remaining longer portion 34 of the release tape 26 extends preferably at least partially over the second surface 20 of the inner tab portion 16 so that the adhesive layer 30 of the release tape 26 is exposed as illustrated in FIG. 2. The release tape 26 assists in securing the closure tape tab to a diaper, wherein the adhesive layer 6 of the proximal end portion 4 is attached to one surface of the diaper ear, e.g., an outer surface, and the longer portion 34 of the release tape 26 is folded over to the opposite side of the diaper ear, e.g., an inner surface thereof, so as to provide a so-called Y-bond. Alternatively, the longer portion 34 of the release tape 26 is initially attached to one surface of the diaper ear, e.g., an inner surface, and the remainder of the closure tape tab is folded over to the opposite side of the diaper ear, e.g., an outer surface, and attached to the diaper ear by means of the adhesive 6 of the proximal end portion 4 of the closure tape tab (as shown in FIGS. 10 and 11).

In the embodiment shown in FIG. 2, the release tape 26 is divided into first and second end sections 35, 37 which are connected by an intermediate section 36. Preferably, a surface of the intermediate section 36 being directed toward the second major surface 20 of the inner tab portion 16 is provided with an adhesive 38. This construction provides an anti-flagging feature, i.e., releasably attaches the longer portion 34 of the release tape 26 to the inner tab portion 16 of the closure tape tab so that a premature release of the release tape can be avoided during handling of the closure tape tab.

Figure 3:
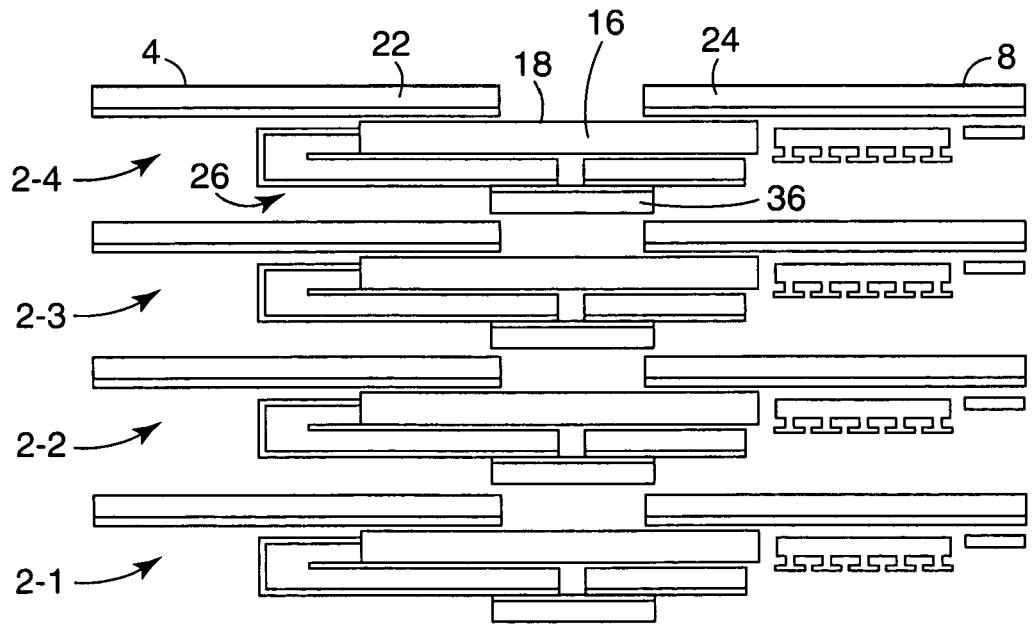
FIG. 3 is a schematic illustration of a winding sequence of the precursor closure tape tab shown in FIG. 2 in a planetary wound configuration.

FIG. 3 illustrates how a precursor closure tape from which the precursor closure tape tab 2 shown in FIG. 2 can be cut, and can be planetary wound so as to provide a roll of precursor closure tape. As shown in FIG. 3, adjacent layers 2-1, 2-2, 2-3, 2-4 of the planetary wound precursor closure tape are arranged such that the intermediate section 36 of the release tape 26 covers the space between the opposing ends 22, 24 of the proximal and distal end portions 4, 8 so that no adhesive contact is established between the release tape 26 and the inner tab portion 16 of an underlying winding of the roll. Accordingly, the precursor closure tape of FIG. 2 can be planetary-wound without the use of any further covering or blanking films which would otherwise be necessary in order to avoid undesired attachment of the release tape 26 to the first major surface 18 of the inner tab portion 16 of an underlying winding.

Figure 4:
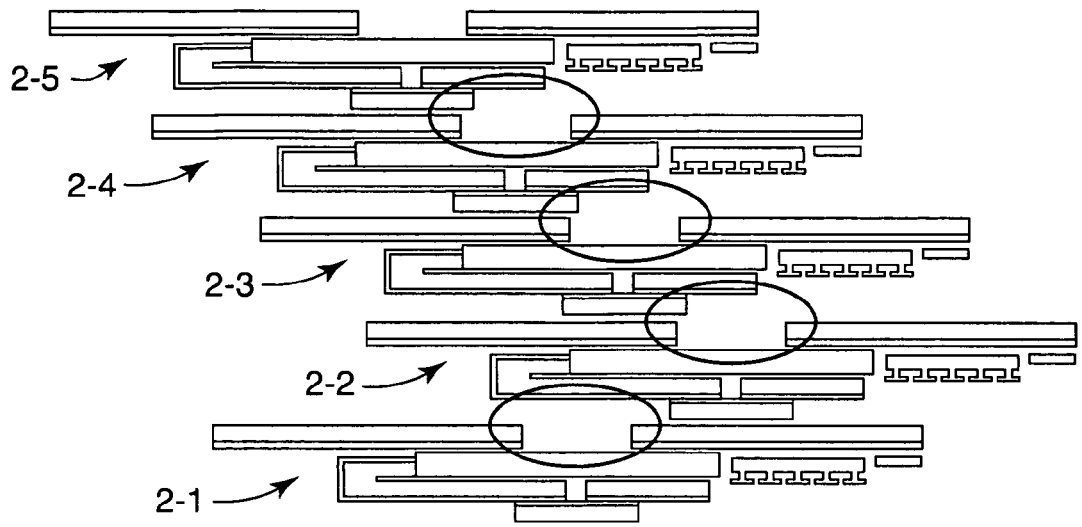
FIG. 4 is a schematic illustration of a winding sequence of the precursor closure tape shown in FIG. 2 in a level-wound configuration.

On the other hand, level winding of the precursor closure tape 2 shown in FIG. 2 would normally not be possible since exposed adhesive 30, 6 and/or 14 of the release tape 26, the proximal end portion 4 and/or the distal end portion 8 might be in contact with the first major surface 18 of the inner tab portion 16 in the space formed between the opposing ends 22, 24 of the proximal and distal end portions, respectively. The areas of potential adhesive contact are marked in FIG. 4 by means of an oval. Accordingly, level winding of the precursor tape 2 of FIG. 2 would not be feasible without any modifications.

Figure 5:
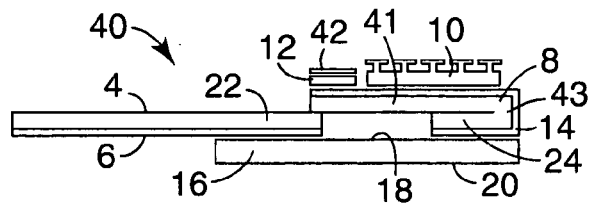
FIG. 5 is a schematic side view of a closure tape tab according to the present invention.

In FIG. 5 a first embodiment of a closure tape tab 40 of the present invention is illustrated. The closure tape tab 40 corresponds in its basic construction to the precursor closure tape tab 2 shown in FIG. 1. However, the distal end portion 8 is folded over by 180° toward the proximal end portion 4 such that the exposed first major surface 18 of the inner tab portion 16 in the space between the opposing ends 22, 24 is covered by the folded part 41 of the distal end portion 8. Preferably, the folding is made along a fold line 43 that is generally aligned or flush with the distal end of the inner tab portion 16. In the embodiment shown in FIG. 5, the folded part 41 of the distal end portion 8 covers said space completely and partially overlaps with the opposing end 22 of the proximal end portion 4. The length of this overlap area is preferably in the range of between 0.5 to 20 mm, more preferably between 1 to 10 mm, and most preferably between 2 and 5 mm. The proximal end portion 4 of the closure tape tab 40 remains unfolded or substantially straight.

Preferably, in the embodiment shown in FIG. 5, the fingerlift 12 is provided with a release coating 42 so that any potential adhesive contact in this area upon winding into a roll is also made releasable. Accordingly, this construction facilitates easy unwinding of the closure tape also in a level-wound roll.

Figure 6:
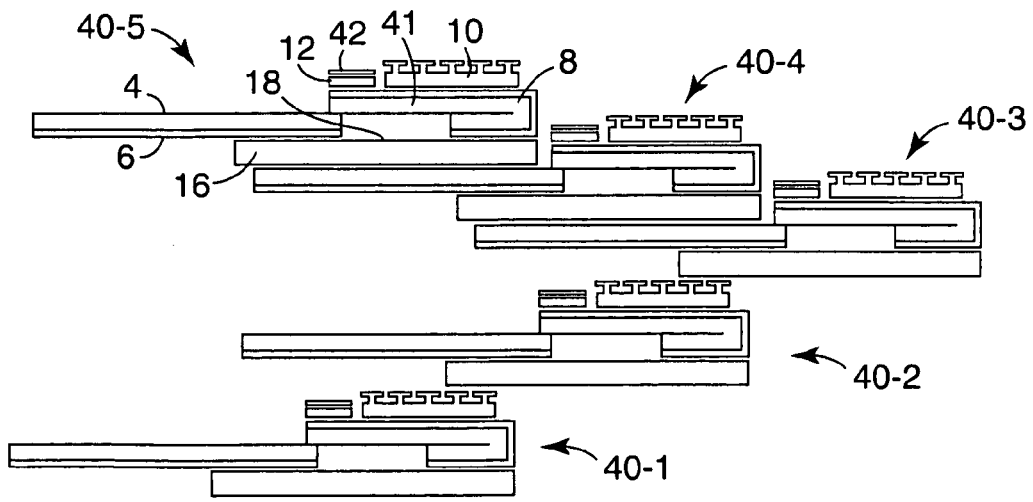
FIG. 6 is a schematic illustration of a winding sequence of the closure tape according to FIG. 5 in a level-wound configuration.

In FIG. 6 a schematic illustration of several layers 40-1, 40-2, 40-3, 40-4, 40-5 of closure tape from which the closure tape tab of FIG. 5 can be cut, is provided showing how the various layers may be arranged arbitrarily one on top of another without undesired adhesive contact. As can clearly be seen in this illustration, adhesive contact between adjacent windings of the closure tape of the present invention in the critical area of the first surface 18 of the inner tab portion 16 is completely avoided by the folded part 41 of the distal end portion 8. Moreover, in the area of the fingerlift 12 the optional release coating 42 prevents blocking during unwinding of the closure tape. Accordingly, the closure tape of the present invention provides a construction that can be level-wound and permits easy unwinding without the danger of adjacent tape layers adhering to one another or damaging components in adjacent layers during unwinding of the roll. In other words, by means of the folding of the closure tape tab laminate as illustrated in FIGS. 5 and 6, the folded part 41 of the distal end portion 8 protects the inner tab portion 16 from exposed adhesive 6 of the proximal end portion 4 that would otherwise come into contact with the inner tab portion when level-wound. Accordingly, a major advantage of the closure tape of the present invention is that it does not require the use of additional components or treatment of the inner tab portion 16 with release coatings etc. to allow the roll to unwind freely.

Figure 7:
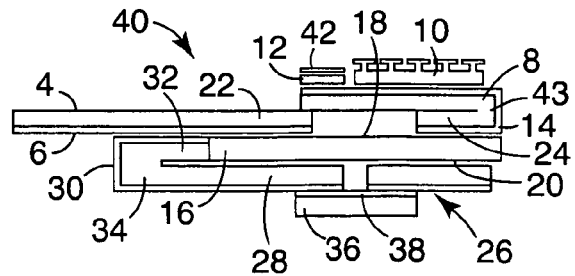
FIG. 7 is a schematic side view of another embodiment of the closure tape tab of the present invention with release tape.

FIG. 7 shows a second embodiment of the closure tape tab 40 of the present invention which can be manufactured from the precursor closure tape tab 2 shown in FIG. 2. As can be seen from FIG. 7, as with the first embodiment of FIG. 5, the distal end portion 8 of the closure tape tab 40 is folded over on itself toward the proximal end portion 4 such that the exposed first major surface 18 of the inner tab portion 16 in the space formed between the opposing ends 22, 24 of the proximal and distal end portions 4, 8 is covered by the folded over part of the distal end portion 8. As with the first embodiment, the distal end portion 8 may slightly overlap with the opposing end 22 of the proximal end portion 4. Similarly, also in this embodiment the fingerlift 12 is provided with a release coating 42 in the form of a low adhesive backsize (LAB) coating. Also in this embodiment, the proximal end portion 4 is not folded.

Figure 8:
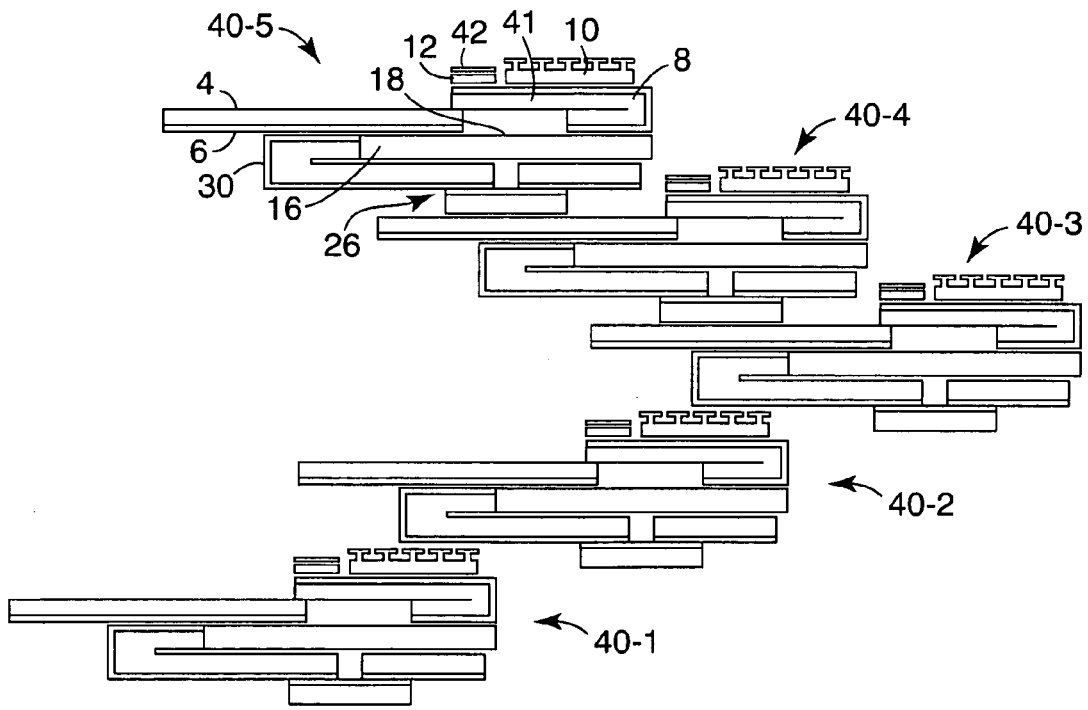
FIG. 8 is a schematic illustration of a winding sequence of the closure tape shown in FIG. 7 in a level-wound configuration.

FIG. 8 schematically illustrates how a closure tape from which the closure tape tab of FIG. 7 can be cut and level-wound. Five layers 40-1, 40-2, 40-3, 40-4, 40-5 of the closure tape are illustrated in FIG. 8 in a level-wound configuration. As can be seen in FIG. 8, by means of the folding of the distal end portion 8 of the closure tape, the folded part 41 of the distal end portion 8 comprising the fastening elements 10 protects the inner tab portion 16 from exposed adhesive 30 of the release tape 26 and the adhesive layer 6 of the proximal end portion 4 that might otherwise come into contact with the inner tab portion 16 in a level-wound roll. In other words, without the folding of the distal end portion 8, level winding would bring the adhesive layer 6 of the proximal end portion 4 and/or the adhesive layer 30 of the release tape 26 into contact with the first major surface 18 of the inner tab portion 16 with the result that the open adhesive layers 6, 30 would adhere to the inner tab portion 16, which might result in delamination of the tape construction and/or blocking of the roll during unwinding of the tape.

The release coating 42 on the fingerlift 12 advantageously facilitates easy unwinding because the fingerlift 12 is also prevented from adhering to the exposed adhesive layers 6, 30 of the proximal end portion 4 and the release tape 26, recepively, during roll building and unwinding. Accordingly, also with the second embodiment illustrated in FIGS. 7 and 8 a closure tape is provided that does not require the use of additional components or treatment of the inner portion 16, e.g., with release coatings or release papers to allow a level-wound roll to unwind freely.

Figure 9:
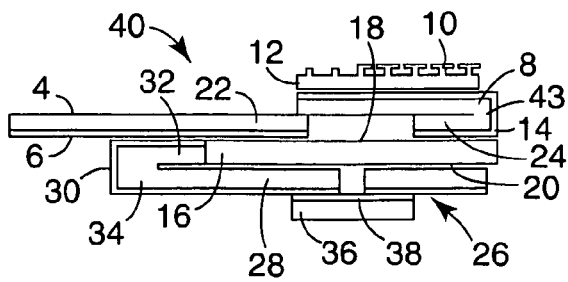
FIG. 9 is a schematic side view of a further embodiment of a closure tape tab according to the present invention.

In FIG. 9 a third embodiment of the closure tape tab 40 of the present invention is illustrated. This embodiment is generally similar to the second embodiment described in connection with FIGS. 7 and 8. The closure tape tab 40 of this embodiment differs from the second embodiment in that it comprises a fingerlift 12a that is provided by crushed hooks of the mechanical fastener component 10 which is attached to the distal end portion 8. The use of such a crushed hook fingerlift 12a has a similar effect as the release coating 42 in that it prevents at least excess adhesion of the adhesive layer 6 of the proximal end portion 4 and the adhesive layer 30 of the release tape 26 of adjacent windings in a level-wound roll. Further details regarding the construction of crushed hook fingerlifts can be found, e.g., in U.S. Pat. No. 5,933,927 (Miller et al.).

Instead of crushing the hooks of the mechanical fastener component 10, the fingerlift 12 can also be provided by rendering the mechanical fastener component 10 ineffective in the area of the fingerlift 12 by any known means. For example, in the area of the fingerlift 12 no hook heads can be formed on the stems protruding from the backing, whereas in the area where fastening properties are desired hook heads are formed on the stems of the mechanical fastener component. It is also possible to erase the hooks at least partially from the mechanical fastener component 10 in the area of the fingerlift 12.

FIG. 10 illustrates how the closure tape tab 40 of the present invention can be attached to a diaper ear. In particular, it is shown in FIG. 10 how the closure tape tab 40 according to the second embodiment of the present invention as illustrated in FIG. 7 is attached to a diaper ear 44 of a disposable diaper. The diaper ear 44 comprises an outer surface 46 and an inner surface 48. As shown in FIG. 10, the proximal end portion 4 is attached to the outer surface 46 of the diaper ear by means of the adhesive layer 6. The closure tape tab 40 is then folded over to the inner surface 48 of the diaper ear 44 so that the release tape 26 can be adhered to the inner surface 48 by means of the exposed adhesive 30 of the release tape 26. In this configuration, the closure tape tab 40 of the present invention is secured to the diaper ear 44 by means of a so-called Y-bond between the adhesives 6 and 30. The user can grasp the distal end portion 8 of the closure tape tab 40, preferably at its fingerlift 12, and unfold the closure tape tab, wherein the proximal end portion 4 and the release tape 26 remain in place on a diaper ear 44, while the inner tab portion 16, which is typically elastic, and the distal end portion 8 are used to fasten the diaper on a body of a person by means of the mechanical fastening element 10 which is brought into engagement with an inter-engaging fastening element provided on a diaper landing zone.

The application of the closure tape tab 40 of the present invention in this folded configuration may also be advantageous from a diaper manufacturing point of view since in the diaper manufacturing line the exposed fastening element 10 can come into contact with the backsheet and/or top sheet of the diaper, which are typically made from non-woven materials, and can therefore assist in preventing premature opening of the folded diaper. Additionally, with the folded configuration according to the present invention the distal end of the closure tape tab may lift slightly during diaper unfolding and be more easily located and grasped by the user.

Figure 10A:
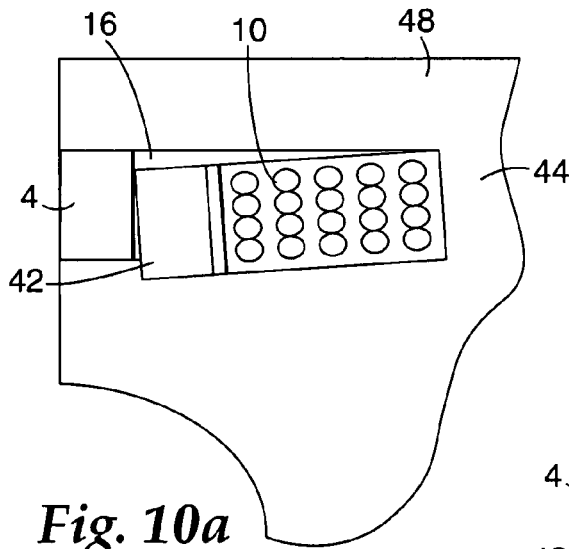
FIG. 10a is a schematic top view showing the closure tape tab of FIG. 7 attached to the diaper ear.
Figure 11A:
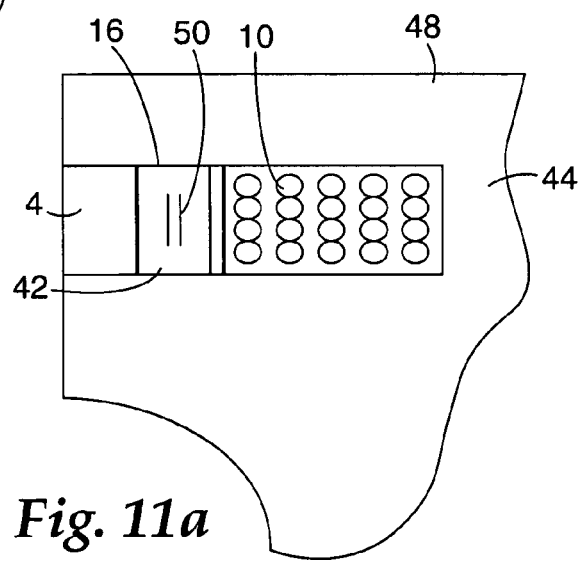
FIG. 11a is a schematic top view on a diaper ear with the closure tape tab of FIG. 11.

In FIG. 10a it is schematically illustrated how the folded part 41 of the distal end portion 8 may undesirably shift on the underlying inner tab portion 16, which is typically only an aesthetic problem. However, in order to eliminate this shifting the closure tape tab 40 of the present invention may comprise a distal end portion 8 that is split apart in the area of the fingerlift 12 to provide a gap 50 as shown in the embodiment of FIG. 11. The fingerlift 12 is adhesively attached to the distal end portion 8 by means of an adhesive layer 52 provided on the fingerlift 12 that allows adhesive contact through the gap 50 to the first major surface 18 of the inner tab portion 16 so as to secure the folded part of the distal end portion 8 to the first major surface 18 of the inner tab portion 16. This is also schematically illustrated in FIG. 11a. Accordingly, an anti-pop open feature or anti-flagging feature is provided by the gap 50 and the adhesive coating on the fingerlift 12.

Also in this embodiment, the closure tape tab 40 of the present invention is provided in a folded form so that during diaper unfolding, prior to use, the free end of the distal end portion may lift slightly and be more easily located by the user. This is not the case in the conventional tab application when a tab lays flat on the top sheet and can be difficult to be located and picked up. Accordingly, the construction of the closure tape tab of the present invention makes the location and gripping of the tab closure system easier for the user.

It is also be possible to provide the closure tape of the present invention in the folded configuration in a roll as shown in FIGS. 5-9, and to pre-open and unfold the tape on the diaper manufacturing line prior to attachment to the diaper. If closure tape unfolding is intended prior to tab cutting and attachment to the diaper, this can be achieved with typically existing roll unwinding and guiding equipment. Additional processing to remove potential folding memory effects in the closure tape in order to allow the closure tape tab to lay flat may be required. This can be achieved through application of suitable web tension during web conveyance after fold opening. The application of heat to relax fold memory at the fold line 43 may also be of benefit.

In order to enhance unwind performance of the closure tape of the present invention it may be advantageous to provide at least the proximal end portion 4 on its surface opposite the adhesive layer 6 with a low adhesive backsize coating (LAB), which may typically be a silicone coating. The same kind of coating may be used on the fingerlift 12.

Accordingly, the present invention provides a closure tape construction that may or may not comprise a release tape, but does in any case not require any additional components or any additional treatment of the typically elastic inner tab portion with any release coatings or release sheetings to allow a level-wound roll of the tape to unwind easily.

The invention claimed is:

1. A folded closure tape tab for an absorbent article, particularly for a disposable diaper, for fastening of the article on the body of a person, comprising a proximal end portion and a distal end portion being connected by an inner tab portion, said inner tab portion having a first major surface and an opposite second major surface, wherein said proximal and distal end portions are connected to said inner tab portion at said first major surface thereof such that opposing ends of said proximal and distal end portions are spaced apart from each other, and wherein said distal end portion is folded toward said proximal end portion such that at least a part of said first major surface of said inner tab portion in said space is covered, wherein said proximal end portion is not folded;

wherein said distal end portion comprises a fingerlift adjacent a free end thereof, wherein said distal end portion is split in the area of said fingerlift to provide a gap, and wherein said fingerlift is adhesively attached to said distal end portion so that adhesive contact between said distal end portion and said inner tab portion can be established through said gap.

2. The closure tape tab according to claim 1, wherein said fingerlift is provided with a release coating.

3. The closure tape tab according to claim 1 further comprising a mechanical fastener component on said distal end portion, wherein said fingerlift is formed by crushed hooks of the mechanical fastener component.

4. The closure tape tab according to claim 1 wherein the distal end portion is folded along a fold line that is generally flush with the distal end of the inner tab portion.

* * * * *